United States Patent
Repka et al.

(10) Patent No.: US 10,448,897 B2
(45) Date of Patent: Oct. 22, 2019

(54) HEART ACTIVITY MEASUREMENT

(71) Applicant: Polar Electro Oy, Kempele (FI)

(72) Inventors: Mikko Repka, Oulu (FI);
Jukka-Tapani Makinen, Oulu (FI);
Juha Sumen, Kempele (FI); Seppo Korkala, Kempele (FI)

(73) Assignee: Polar Electro Oy, Kempele (FI)

( * ) Notice: Subject to any disclaimer, the term of this patent is extended or adjusted under 35 U.S.C. 154(b) by 761 days.

(21) Appl. No.: 14/631,501

(22) Filed: Feb. 25, 2015

(65) Prior Publication Data

US 2016/0242698 A1 Aug. 25, 2016

(51) Int. Cl.
*A61B 5/00* (2006.01)
*A61B 5/02* (2006.01)
(Continued)

(52) U.S. Cl.
CPC .......... *A61B 5/7214* (2013.01); *A61B 5/0059* (2013.01); *A61B 5/02* (2013.01); *A61B 5/02416* (2013.01); *A61B 5/681* (2013.01); *A61B 5/6844* (2013.01); *A61B 5/721* (2013.01); *A61B 5/7207* (2013.01); *A61B 5/0261* (2013.01); *A61B 5/0265* (2013.01); *A61B 5/02427* (2013.01); *A61B 5/0402* (2013.01); *A61B 5/0531* (2013.01); *A61B 5/6815* (2013.01);
(Continued)

(58) Field of Classification Search
CPC ... A61B 5/6815; A61B 5/6823; A61B 5/6824; A61B 5/6844; A61B 5/7207; A61B 5/721; A61B 5/7214; A63B 2230/04; G02B 27/0075
See application file for complete search history.

(56) References Cited

U.S. PATENT DOCUMENTS 5,983,120 A * 11/1999 Groner ................. A61B 5/0261
356/364
2008/0097221 A1* 4/2008 Florian .............. A61B 5/02433
600/476
(Continued)

FOREIGN PATENT DOCUMENTS

EP 1 297 784 A1 4/2003
EP 2 612 594 A2 7/2013

OTHER PUBLICATIONS

Wang et al, "Exploiting Spatial Redundancy of Image Sensor for Motion Robust rPPG," IEEE Transactions on Biomedical Engineering, vol. 62(2); pp. 415-425 (Feb. 1, 2015).
(Continued)

*Primary Examiner* — Katherine L Fernandez (74) *Attorney, Agent, or Firm* — Fisherbroyles, LLP (57) ABSTRACT

A method includes: obtaining, by an apparatus, instantaneous images from an optical heart activity sensor, wherein the instantaneous images characterize a heart activity data of a user; obtaining information about spatial shifts of a measuring area of the optical heart activity sensor in relation to a body tissue of the user; determining effect of the spatial shifts in the instantaneous images based on the information about the spatial shifts; enhancing the instantaneous images by decreasing the effect of the spatial shifts in the instantaneous images; and processing the enhanced instantaneous images into the heart activity data of the user.

20 Claims, 5 Drawing Sheets

(51) Int. Cl.
*A61B 5/024* (2006.01)
*G02B 27/00* (2006.01)
*A61B 5/026* (2006.01)
*A61B 5/0265* (2006.01)
*A61B 5/0402* (2006.01)
*A61B 5/053* (2006.01)

(52) U.S. Cl.
CPC ........... *A61B 5/6823* (2013.01); *A61B 5/6824* (2013.01); *A61B 2562/0219* (2013.01); *A61B 2562/0223* (2013.01); *A63B 2230/04* (2013.01); *G02B 27/0075* (2013.01)

(56) References Cited

U.S. PATENT DOCUMENTS

| | | | | |
|---|---|---|---|---|
| 2008/0130103 | A1* | 6/2008 | Hara et al. | 359/369 |
| 2013/0072771 | A1* | 3/2013 | Gu | A61B 5/0205 |
| | | | | 600/324 |
| 2014/0305204 | A1* | 10/2014 | Hong | A63B 71/06 |
| | | | | 73/504.08 |
| 2015/0005613 | A1* | 1/2015 | Kim | A61B 5/0095 |
| | | | | 600/407 |

OTHER PUBLICATIONS

European Search Report, Application No. EP16155211, dated Jul. 28, 2016.

* cited by examiner

Fig. 1

210 OBTAINING, BY AN APPARATUS, FROM AN OPTICAL HEART ACTIVITY SENSOR INSTANTANEOUS IMAGES CHARACTERIZING HEART ACTIVITY DATA OF A USER

220 OBTAINING INFORMATION ABOUT SPATIAL SHIFTS OF A MEASURING AREA OF THE OPTICAL HEART ACTIVITY SENSOR IN RELATION TO A BODY TISSUE OF THE USER

230 DETERMINING EFFECT OF THE SPATIAL SHIFTS IN THE INSTANTANEOUS IMAGES BASED ON THE INFORMATION ABOUT THE SPATIAL SHIFTS

240 ENHANCING THE INSTANTANEOUS IMAGES BY DECREASING THE EFFECT OF THE SPATIAL SHIFTS IN THE INSTANTANEOUS IMAGES

250 PROCESSING THE ENHANCED INSTANTANEOUS IMAGES INTO THE HEART ACTIVITY DATA OF THE USER

HEART ACTIVITY MEASUREMENT

BACKGROUND

Field

The invention relates generally to heart activity measurement. More particularly, the present invention relates to enhancing the heart activity measurement.

Description of the Related Art

Measuring heart activity has become easier, not only during training, but also when users are performing their everyday activities. Thus, a demand for solutions making the heart activity monitoring more effortless has risen. Making the heart activity measurement more robust may increase the effortlessness of the measurement as then the greatest attention may be given to the task at hand.

SUMMARY

According to an aspect, there is provided an apparatus for measuring heart activity data of a user, the apparatus comprising: at least one sensor comprising an optical heart activity sensor, wherein the optical heart activity sensor comprises a measuring head and a matrix detector, wherein the measuring head is configured to be directed towards a body tissue of the user and to form instantaneous images on the matrix detector from a light propagated through the body tissue of the user, wherein the matrix detector is configured to detect the instantaneous images, and wherein the at least one sensor is further configured to detect spatial shifts of the measuring head in relation to the body tissue of the user, a processing circuitry configured to receive the instantaneous images from the optical heart activity sensor, to determine effect of the spatial shifts in the instantaneous images based on the detected spatial shifts, and to process the instantaneous images into the heart activity data of the user, and a controller configured to enhance the heart activity data by decreasing the effect of the spatial shifts in the instantaneous images.

According to an aspect, there is provided a method comprising: obtaining, by an apparatus, instantaneous images from an optical heart activity sensor, wherein the instantaneous images characterize a heart activity data of a user, obtaining information about spatial shifts of a measuring area of the optical heart activity sensor in relation to a body tissue of the user, determining effect of the spatial shifts in the instantaneous images based on the information about the spatial shifts, enhancing the instantaneous images by decreasing the effect of the spatial shifts in the instantaneous images, and processing the enhanced instantaneous images into the heart activity data of the user.

According to an aspect, there is provided a computer program product embodied on a non-transitory distribution medium readable by a computer and comprising program instructions which, when loaded into an apparatus, execute a computer process comprising: obtaining instantaneous images from an optical heart activity sensor, wherein the instantaneous images characterize a heart activity data of a user, obtaining information about spatial shifts of a measuring area of the optical heart activity sensor in relation to a body tissue of the user, determining effect of the spatial shifts in the instantaneous images based on the information about the spatial shifts, enhancing the instantaneous images by decreasing the effect of the spatial shifts in the instantaneous images, and processing the enhanced instantaneous images into the heart activity data of the user.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

Embodiments of the present invention are described below, by way of example only, with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
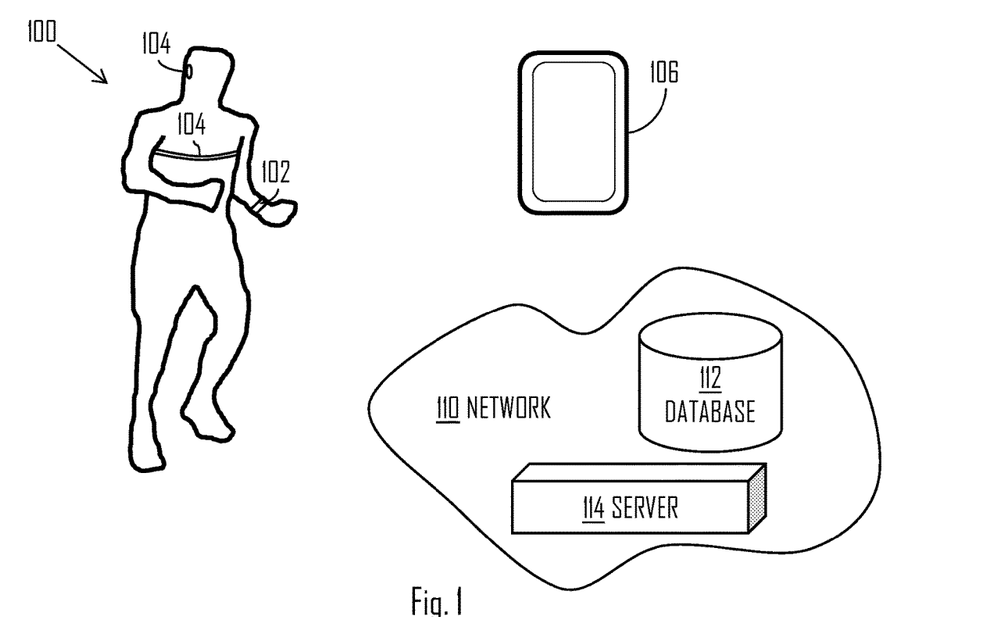
FIG. 1 illustrates a heart activity measurement system to which embodiments of the invention may be applied.

FIG. 1 illustrates a heart activity measurement system to which embodiments of the invention may be applied. Referring to FIG. 1, heart activity of a user 100 may be monitored by the user 100 using an activity tracker apparatus 102. The activity tracker apparatus 102 may be a portable or wearable electronic device, such as a wrist device 102. The wrist device 102 may comprise a heart activity circuitry configured to determine user's 100 heart activity, such as heart rate for example. The heart activity circuitry may comprise an optical heart activity sensor, such as a PPG (photoplethysmography) sensor, configured to measure heart activity of the user 100. The optical heart activity sensor may detect the user's 100 heart activity by optical heart rate measurement, which may comprise sending a light beam towards body tissue of the user, and measuring the bounced and/or emitted light from the body tissue of the user 100. The body tissue of the user 100 may be, for example, skin of the user 100. The light beam may alter when travelling through the user's 100 veins and the alterations may be detected by the optical heart rate activity sensor. By using the detected data, the wrist device 102, may determine user's 100 heart activity, such as heart rate for example.

The heart activity circuitry may comprise a bioimpedance sensor, wherein the bioimpedance sensor is configured to measure user's 100 heart activity. The bioimpedance measurement may be based on transmitting a radio signal into user's 100 skin, and observing changes in the radio signal due to impedance changes caused by, for example, blood volume changes. Thus, the user's 100 heart activity, such as heart rate, may be determined by the heart activity circuitry from the data produced by the bioimpedance sensor.

Further, besides these types of heart activity sensors, also other types of biosignal measurement sensors may be embedded into the heart activity circuitry. These types include but are not limited to the following: a Laser Doppler-based blood flow sensor, a magnetic blood flow sensor, an Electromechanical Film (EMFi) pulse sensor, a polarization blood flow sensor.

The wrist device 102 may comprise a motion circuitry configured to measure motion of the wrist device 102, wherein the motion circuitry may comprise one or more motion sensor(s). The motion circuitry may be configured to measure the motion of the wrist device 102 in relation to the body tissue of the user 100. Thus, the motion circuitry may provide information about the connection of the wrist device 102 to the wrist of the user 100.

Further, the motion circuitry may be configured to detect motion induced by the user 100 to the wrist device 102 by moving hand in which the user 100 wears the wrist device 102. The motion circuitry may use other motion data, such as location data of the user, to determine user's 100 motion.

In an embodiment, the motion sensor(s) comprise at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the heart activity measurement system may further comprise the external sensor device(s) 104 used by the user 100. The external sensor device(s) 104 may comprise sensors, such as a heart rate transmitter, a stride sensor, a positioning sensor, a cadence sensor and a power sensor, to mention a few. The heart rate transmitter may comprise at least one electrical, optical and/or bioimpedance sensor to measure user's 100 heart activity. The electrical sensor(s) may be, for example, based on Electrocardiography (EKG) measurement. The positioning sensor may comprise a GPS, a magnetometer and/or a Bluetooth sensor. Thus, the positioning may be based on, for example, GPS location and/or Bluetooth location. The magnetometer may provide direction data based on magnetic fields on earth and/or inside structures.

The external sensor device(s) 104 may be attached to the user 100. Thus, for example the optical heart activity sensor may be attached to the body tissue of the user 100. Further, the external sensor device(s) 104 may detect the motion of the external sensor device(s) 104 in relation to the body tissue of the user 100. This may be achieved by using motion sensor(s), and heart activity sensor(s) as described later in more detail.

The external sensor device(s) 104 may comprise a head sensor, wherein the head sensor may be configured to measure heart activity of the user 100. The head sensor may be, for example, an ear sensor which may be placed within the user's 100 ear. The placement may be similar to placing earplug headphones. The head sensor may utilize optical measurement and/or bioimpendace measurement for the heart rate measurement, for example. In an embodiment, the ear sensor is an in-ear sensor.

The external sensor device(s) 104 may transmit the sensor data to the wrist device 102, to a portable electronic device 106 and/or to a server 114, residing in a network 110, of the heart activity measurement system. The portable electronic device 106 may be a mobile phone, a smart phone, a palm device, a tablet computer, phablet or a portable digital assistant, for example. The wrist device 102, the portable electronic device 106 and/or the server 114 may receive the sensor data. Similarly, the wrist device 102 may transmit the heart activity data, provided by the heart activity circuitry, and/or the motion sensor data, provided by the motion sensor, to the portable electronic device 106 and/or the server 114. The wrist device 102, the portable electronic device 106 and/or the server 114 may comprise at least one processor configured to process the received external sensor data, the heart activity data and/or the motion data into a set of metrics describing the user's 100 physical activity, such as heart rate of the user 100.

The external sensor device(s) 104, the wrist device 102, the portable electronic device 106 and/or the server 114 may further comprise a communication circuitry, such as wireless communication circuitry, configured to enable sensor data transfer between the external sensor device(s) 104, wrist device 102, portable electronic device 106 and/or the server 114.

In an embodiment, the external sensor device(s) 104 comprise at least one external sensor device.

Further, the wrist device 102 and/or the portable electronic device 106 may comprise a memory, wherein the memory may be used by the devices to store the data from different sensor devices. The server 114 may use a database 112, such as a training database, to store the said data. The database 112 may reside in the network 110.

In an embodiment, the external sensor device(s) 104 are comprised in the wrist device 102.

In an embodiment, the wrist device 102 further comprises at least one of the following sensors: a temperature sensor, a positioning sensor and a pressure sensor. The positioning sensor may utilize GPS and/or Bluetooth information for locating the user 100. Further, the positioning sensor may comprise a magnetometer.

The described heart activity measurement system may enable the user to track the heart activity from different devices. For example, the wrist device 102 may be used during a physical exercise, wherein the heart activity information may be stored to the memory of the wrist device 102. The heart activity information may be transferred and stored to the portable electronic device 106 and/or to the server 114, where it may be viewed during the exercise and/or after the exercise. Further, the database 112 may comprise information from other users. This information may be usable by the user 100 in order to, for example, benchmark user's 100 physical progress.

The reliability of the heart activity measurement may sometimes be disturbed by effect of spatial shifts which may be caused by, for example, movement of the heart activity sensor(s) in relation to the body tissue of the user 100. Decreasing or removing the effect of the spatial shifts may enhance the reliability of the heart activity measurement. There is provided a solution for enhancing the heart activity measurement by decreasing the effect of the spatial shifts of said measurement.

Figure 2:
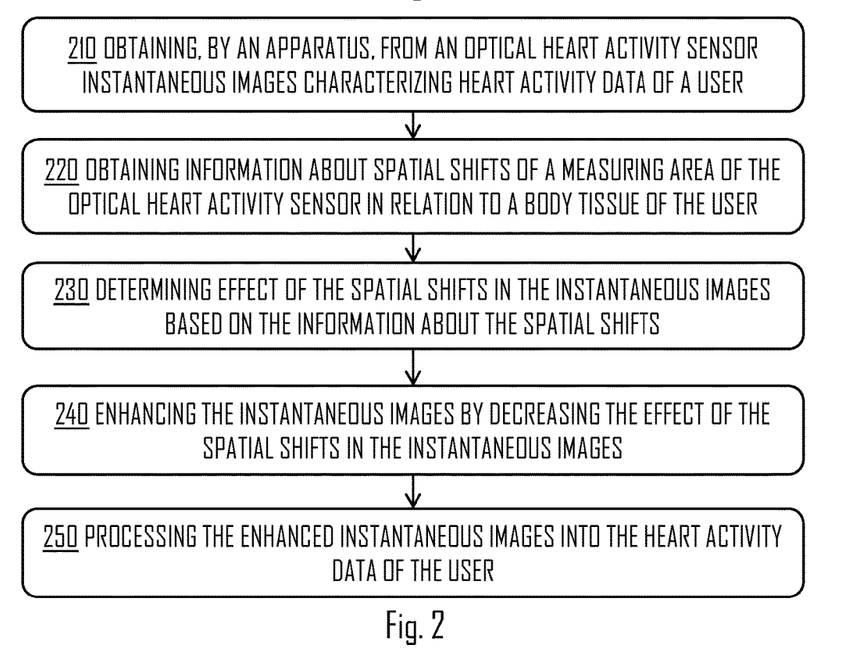
FIG. 2 illustrates a block diagram according to an embodiment of the invention.

FIG. 2 illustrates a block diagram according to an embodiment of the invention. Referring to FIG. 2, in step 210, an apparatus, such as the wrist device 102, the portable electronic device 106, the server 114 and/or the external sensor device(s) 104, may obtain instantaneous images characterizing a heart activity data of the user 100. The instantaneous images may be obtained and/or received from an optical heart activity sensor, for example. As described earlier in relation to FIG. 1, the optical heart activity sensor may be comprised in the wrist device 102 and/or the external sensor device(s) 104. Further, the instantaneous images may be received from one or more sources, sensor(s) that is. This may allow the use of more than one sensor for the measurement.

The instantaneous images may be understood as samples detected by the optical heart activity sensor from a light propagated through the body tissue of the user 100. The instantaneous images may each characterize the user's 100 heart activity data at a certain time. The instantaneous images may be detected by a matrix detector, for example. The matrix detector may be comprised in the optical heart activity sensor.

In step 220, the apparatus may obtain information about spatial shifts of a measuring area of the optical heart activity sensor in relation to the body tissue of the user 100. The information about the spatial shifts may be received from the optical heart activity sensor and/or from the motion sensor(s). The measuring area may be an area which is directed towards the body tissue of the user 100. The measuring area may be at least partly in physical contact with the body tissue of the user 100. The spatial shifts may mean movement of the measuring area in relation to the body tissue of the user. For example, a wrist device 102 may move in relation to the body tissue, and thus cause the measuring area to move also. This may cause inaccuracy to the heart activity measurement.

In step 230, the apparatus may determine effect of the spatial shifts in the instantaneous images based on the information about the spatial shifts received in step 220. The effect of the spatial shifts may be detected from data provided by the optical heart activity sensor and/or the motion sensor(s). For example, in the case of optical heart activity sensor, said sensor may have spatial observation ability allowing the optical heart activity sensor to provide information about the spatial shifts from where the spatial shifts of the optical heart activity sensor in relation to the body tissue may be determined. It may be possible to compare instantaneous images in order to reveal the effect of the spatial shifts in the instantaneous images. Let us imagine that two instantaneous images are obtained by the apparatus, and that the measuring area moves in relation to the body tissue of the user 100 between said two instantaneous images. The movement of the measuring area may cause spatial differences between said two instantaneous images. By comparing the said two images, it may be possible to determine the effect of the spatial shifts and/or the movement of the measuring area in relation to the body tissue of the user 100. In another example, the motion sensor(s) may provide information about the spatial shifts from where the spatial shifts, of the measuring area of the optical heart activity sensor, in relation to the body tissue of the user 100 may be determined. These described examples may be used together to enhance the determination of the effect of the spatial shifts. Naturally, they may also be used separately. However, it may be beneficial to use both data from the optical heart activity sensor(s) and the motion sensor(s).

In step 240, the apparatus may enhance the instantaneous images by decreasing the effect of the spatial shifts in the instantaneous images. The decreasing of the effect of the spatial shifts may be done digitally and/or mechanically. For example, the instantaneous images may be processed digitally to decrease the effect of the spatial shifts from the data. Also mechanical actuators may be used to control angle of the optical heart activity sensor in relation to the body tissue and/or to modify optical path of received light in the optical heart activity sensor, for example. When the decreasing is achieved by digital processing, it may be based on the detected effects of the spatial shifts, wherein the detected effects of the spatial shifts are determined from instantaneous images and/or the data from the motion sensor(s). For example, instantaneous image(s) may be relocated virtually to decrease the effect of the spatial shift. The relocation may correspond to the determined effect of the spatial shift on the instantaneous image(s). The digital processing may be discussed later in more detail. It needs to be noted that although instantaneous images are discussed in a plural form, each instantaneous image may still be enhanced, using said methods, individually.

In an embodiment, the digital processing comprises virtually relocating at least one instantaneous image. The relocating may mean that the at least one instantaneous image is virtually positioned so that the at least one instantaneous image may be virtually at the same position as the other instantaneous images. Thus, the effect caused by the spatial shifts may be reduced, decreased and/or canceled.

In an embodiment, the decreasing of the effect of the spatial shifts comprises canceling the effect of the spatial shifts. Therefore, the heart activity measurement may be enhanced by providing a correction that corresponds to the effect of the spatial shifts, thus canceling the effect of the spatial shifts on the instantaneous images. In a way, it may be understood that the spatial shifts are countered using digital and/or mechanical correction mechanisms.

In step 250, the apparatus may process the enhanced instantaneous images into the heart activity data of the user 100. It needs to be understood that the steps 220, 230, 240 may happen after the forming and/or processing of the heart activity data of the user 100. Therefore, it may be possible to first process the instantaneous images into the heart activity data and then enhance the heart activity data by decreasing the effect of the spatial shifts from the instantaneous images. In some cases, it may even be possible to form the heart activity data, and to enhance it as a post-training processing. In such cases, the information about the spatial shifts may be obtained after the training, for example. The heart activity data may comprise heart rate of the user and/or heart rate variability (HRV), to name a few. HRV may reveal the changes in time between consecutive heart beats.

Figure 3:
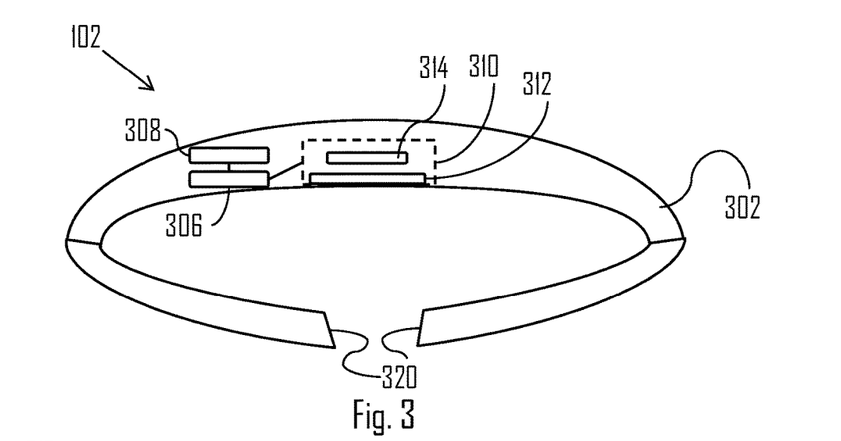
FIG. 3 illustrates an apparatus according to an embodiment of the invention.

FIG. 3 illustrates the apparatus according to an embodiment of the invention. The apparatus may be the wrist device 102, for example. The apparatus may be configured to be attached on a body tissue of the user 100. Thus, the apparatus may also be one of the external sensor device(s) 104. In sake of simplicity let us now describe some of the embodiments in relation to the wrist device 102.

Referring to FIG. 3, the wrist device may comprise at least one sensor 310 comprising an optical heart activity sensor 312, wherein the optical heart activity sensor 312 comprises a measuring head and the matrix detector, wherein the measuring head is configured to be directed towards the body tissue of the user 100 and to form the instantaneous images on the matrix detector from a light propagated through the body tissue of the user 100, wherein the matrix detector is configured to detect the instantaneous images, and wherein the at least one sensor is further configured to detect spatial shifts of the measuring head in relation to the body tissue of the user 100. The spatial shifts may indicate if the measuring head is in a desired position and/or alignment in relation to the body tissue of the user 100. If the position or alignment is unsatisfactory, the optical heart activity data may be needed to enhance.

The measuring head may be adapted and dimensioned to be in physical connection with the user 100. The connection may be partial, for example. The measuring head may be in a certain position and/or alignment in relation to the body tissue of the user 100. In an embodiment, the measuring head is and/or is comprised in the measuring area introduced in relation to FIG. 2.

The wrist device 102 may further comprise a processing circuitry 306 configured to receive the instantaneous images from the optical heart activity sensor 312, to determine effect of the spatial shifts in the instantaneous images based on the detected spatial shifts, and to process the instantaneous images into the heart activity data of the user. The processing circuitry 306 may determine the effect of the spatial shifts from the detected spatial shifts provided by the optical heart activity sensor 312 and/or a motion sensor 314.

Further, the wrist device 102 may comprise a controller 308 configured to enhance the heart activity data by decreasing the effect of the spatial shifts in the instantaneous images. The controller 308 may decrease the effect of the spatial shifts by digital processing and/or by mechanical actuator(s). The controller 308 may perform the functions described in relation to the step 240 of FIG. 2.

Still referring to FIG. 3, the wrist device 102 may comprise a body 302 adapted to be fitted around a wrist of the user 100. The wrist device 102 may further comprise one or more connection members 320 to secure the wrist device 102 around the wrist.

In an embodiment, the body 302 is made of, at least partly, elastic material, thus enabling the wrist device 102 to be attached around the wrist tightly. The connection members 320 may not necessarily have to be connected together in order to fasten the wrist device 102 securely. It may be possible that the form and/or material of at least one of body 302, connection members 320 produces force towards the wrist of the user, thus providing secure fastening.

Let us now take a closer look on the optical heart activity sensor 312 by looking at some embodiments of FIGS. 4A to 4F. As said before, the optical heart activity sensor 312 may be comprised in the wrist device 102 and/or the external sensor device(s) 104.

Figure 4A:
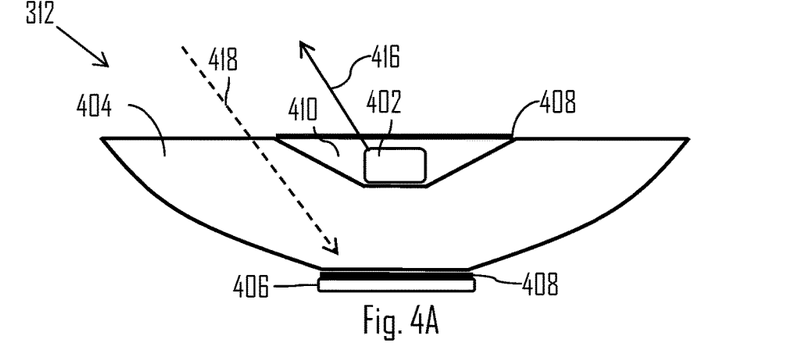
FIGS. 4A to 4F illustrate some embodiments of the invention.

FIG. 4A illustrates a cross-section of the optical heart activity sensor 312. Referring to FIG. 4A, the optical heart activity sensor 312 may comprise at least one light emitting diode (LED) 402 configured to transmit light 416 in to the body tissue of the user 100, an imaging lens 404 configured to receive light 418 propagated through the body tissue of the user 100, and a detector 406, wherein the imaging lens 404 is configured to form the instantaneous images on the detector 406 from the received propagated light 418.

In an embodiment, the measuring head of the optical heart activity sensor 312 comprises the at least one LED 402 configured to transmit the light 416 in to the body tissue of the user 100, and an imaging lens 404 configured to receive the light 418 propagated through the body tissue of the user 100, wherein the imaging lens 404 is configured to form the instantaneous images on the detector 406 from the received propagated light 418.

The light 418 may be emitted from the body tissue to which the light 416 is transmitted. The imaging lens 404 may average the received light 418 to the detector 406 as the light 418 may be gathered from a certain area compared to a point-like light beam. Thus, variations in the received light 418, caused by, for example, moles and/or scars, may not have such a great effect on the measurement. This may make the measurement more robust.

In an embodiment, the at least one LED 402 and/or the detector 406 are situated on an optical axis of the imaging lens 404.

In an embodiment, the at least one LED 402 is replaced by some other light source. This may mean that the light transmitted to the body tissue may be produced by some other light source than LED(s).

The detector 406 may be a photodiode and/or a matrix detector, for example. Using the matrix detector may provide the optical heart activity sensor 312 the spatial observation ability. The matrix detector may be able to detect details from the body tissue of the user 100, for example. However, other solutions than the photodiode and/or the matrix detector may be possible.

The imaging lens 404 may comprise a cavity 410 for the at least one LED 402. The imaging lens 404 may be formed so that the cavity 410 is conical. The walls 412 of the cavity may be mirror coated in order to direct the light 416 towards the body tissue. The cavity 410 may further be filled with clear material, such as ultraviolet curable adhesive, eboxy and/or silicone paster to protect the at least one LED 402 from external forces. The clear material may enable light to travel without substantial obstacles to the body tissue.

The cavity 410 may function as a focuser, enabling the light 416 to enter the body tissue at a certain angle, and thus allowing the light 416 to better penetrate the body tissue to a certain depth. Without the cavity 410, the light 416 may be distributed to a wider area, depending on the configuration of the at least one LED 402. This may not be energy efficient, as light may be wasted to areas where it is not required.

In an embodiment, the lens 404, when directed towards and/or against the body tissue of the user 100, encapsulates the at least one LED 402 against the body tissue of the user 100. Thus, the cavity 410 may be against the body tissue of the user 100, and thus body tissue of the user 100 may act as one wall of the cavity.

In an embodiment, the at least one LED 402 may comprise a directing member configured to direct the light transmitted by the at least one LED 402 towards the body tissue at a certain angle. The certain angle may be a desired angle.

In an embodiment, the imaging lens 404 is made, at least partly, of polyethylene terephthalate (PET). The PET used may be clear to enable light to travel without being substantially disturbed.

Still referring to FIG. 4A, the light received and/or transmitted may be polarized. To achieve this, the optical heart activity sensor 312 may comprise at least one polarization member 408 arranged to polarize at least one of the transmitted light 416 in to the body tissue of the user 100, the received light 418 propagated through the body tissue of the user 100. The polarization member 408 polarizing the received light 418 may, for example, be arranged to be on top of the detector 406. The polarization member 408 polarizing the transmitted light 416 may, for example, be arranged to be on top of the at least one LED 402, thus polarizing light before it enters the body tissue of the user 100.

Figure 4B:
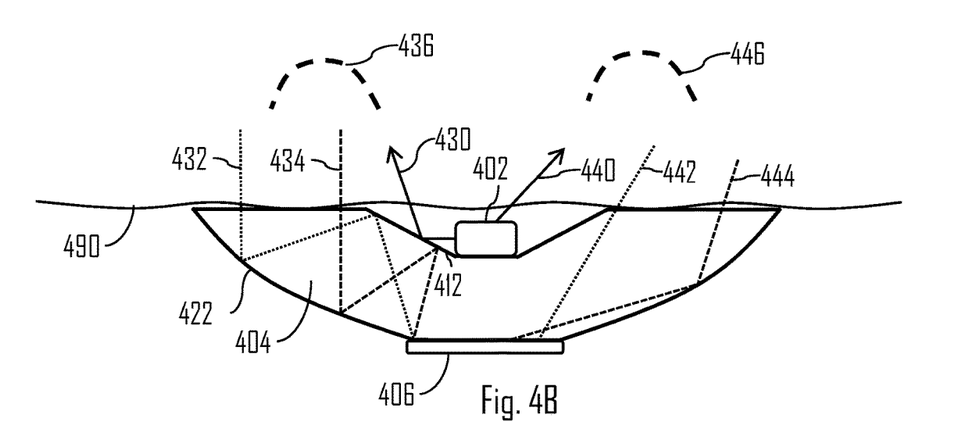

FIG. 4B illustrates a cross-section of the optical heart activity sensor 312. In FIG. 4B, the travelling of light in the imaging lens 404 may be illustrated in more detail. As was shown in FIG. 4A, the light 418 may travel to the detector 406 directly from the body tissue of the user 100. The imaging lens 404 may refract the received light 418. However, the refracting may be minimal, and/or its effect may be countered by refracting when the received light leaves the imaging lens 404 before hitting and/or reaching the detector 406. Referring to FIG. 4B, the transmitted light 430, 440 by the at least one LED may enter the body tissue 490 of the user 100 by different paths. The light 440 may enter the body tissue 490 directly, and the light 430 may reflect from the walls 412 of the cavity 410.

In an embodiment, the walls 412 are mirror coated to enhance the reflection ability.

The light 430, 440 may scatter 436, 446 in the body tissue 490. The scattering 436, 446 may be understood as scattering paths 436, 446. At least some of the light 430, 440 may be collected by the imaging lens 404. The collected light 432, 434, 442, 444 may enter the imaging lens 404 from different parts of the imaging lens. It needs to be understood that the imaging lens 404 may surround the at least one LED 402, and thus it may collect the light from a ring area around the at least one LED 402. Further, the cavity 410 may be conical in cross-sectional illustration, but it may also be circular.

The imaging lens 404 may comprise at least one parabolic reflector 422. The parabolic reflector may be mirror coated, and reflect light towards the detector 406 as shown with dash line 444. The parabolic reflector 422 may also direct light towards the walls 412, as shown with lines 432, 434. The walls 412 may further direct the light to the detector 406. The parabolic reflector 422 may be formed so that light received with certain angle may be directed, using the walls 412, on a certain spot on the detector. Thus, light received from the certain angle and from different area(s) may be directed on the certain spot. Light received from different angles may be directed to a second certain spot on the detector 406. Also, light may travel directly to the detector without being reflected by the walls 412 and/or the parabolic reflector 422. Further, the walls 412 may be mirror coated from both inside and outside.

In an embodiment, the at least one parabolic reflector 422 is circular. This may mean that the at least one parabolic reflector 422 forms a circle around the at least one LED 402 as shown in FIG. 4. The at least one parabolic reflector 422 may be comprised in the outer-wall of the imaging lens 404. The outer-wall may act as the at least one parabolic reflector. As the outer-wall may have two sides, inside and outside, the inside may act as the at least one parabolic reflector, and comprise, for example, mirror-coating. Further, the outside may act as a barrier for external light, thus preventing external light coming into the system.

The imaging lens 404 may collect light from a substantially large area, and direct the light to the detector 406 averaging, for example, the received light 432, 434. The at least one parabolic reflector 422 may direct and/or focus the light to the detector 406.

In an embodiment, the walls 412 and the at least one parabolic reflector 422 direct and/or focus the light to the detector 406.

Averaging may be beneficial as there may be, for example, a mold in a measuring area of the body tissue 490 producing faulty measurements. By averaging the light on the detector 406, the measurement may become more robust. Thus, the measurement may also endure more effect of the spatial shifts, and decrease the effect of the spatial shifts.

In an embodiment, the imaging lens 404 is configured to be placed against the body tissue 490. Therefore, the imaging lens 404 may encapsulate the at least one LED 402 against body tissue of the user 100. The encapsulation may help to prevent external light coming into the system, and disturb the measurement.

Figure 4C:
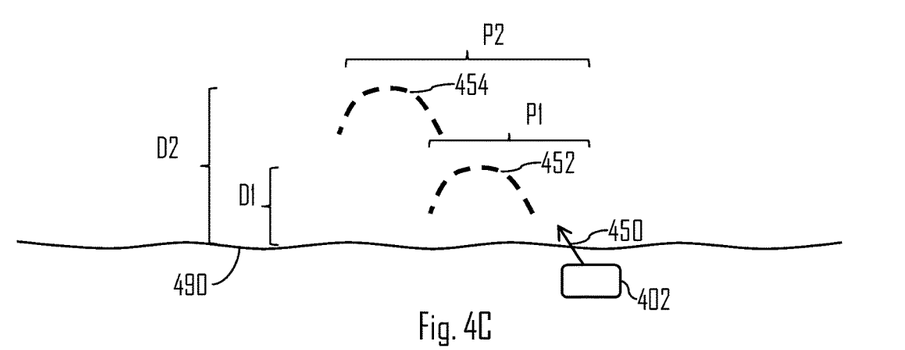

FIG. 4C illustrates an embodiment of the invention. Referring to FIG. 4C, the at least one LED 402 may transmit light 450 in to the body tissue 490. The at least one LED may be configured to transmit the light 450 in to the body tissue 490 in pulses. This may, for example, save energy, and thus increase battery life of the apparatus. Similarly, the detector 406 may be switched on and off according to the pulse pattern.

The light 450 transmitted may comprise more than one wavelength. In an embodiment, light 450 transmitted by the at least one LED 402 comprises two or more wavelengths. For example, the at least one LED 402 may transmit first wavelength which may have a first scatter path 452. The first scatter path may be of certain length P1 and of certain depth D1. Therefore, the first wavelength may penetrate the body tissue 490 to the depth D1. Further, the distance P1 may be understood as the distance between the light of the first wavelength entering the body tissue 490 and exiting the body tissue 490. Similarly, a second wavelength may have a second scatter path 454 having a length P2 and a depth D2. For green light the distance may be circa 3 millimeters (mm), for example. The distances P1, P2, D1, D2 presented here may illustrate average distances for different wavelengths of light. However, said distances may also vary for a certain wavelength as the body tissue may not be homogeneous, and different parts of the measurement systems may comprise imperfections caused by, for example, manufacturing tolerances.

It needs to be understood that the more than one wavelength may be transmitted simultaneously and/or in pulses to the body tissue 490. The different wavelengths may be thus sent in different time. It may be beneficial to use more than one wavelength in the transmitted light 450. For example, red light may work better in cold conditions compared to green light, as blood volume changes in veins may be easier to detect with the red light in such conditions. Further, effect of the spatial shifts may be decreased using two or more wavelengths by comparing the results of the two. This may be explained later in more detail.

Figure 4D:
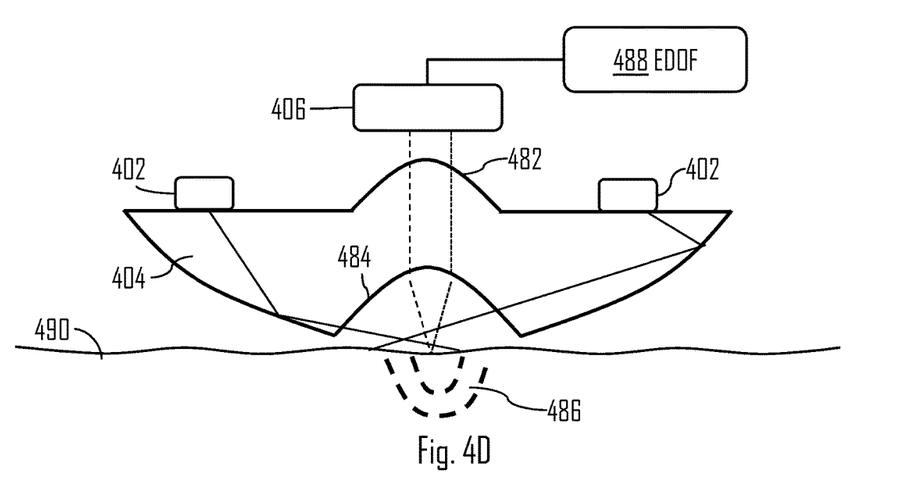

FIG. 4D illustrates a cross-section of the optical heart activity sensor according to an embodiment of the invention. Referring to FIG. 4D, the optical heart activity sensor 312 may comprise the imaging lens 404, wherein the imaging lens 404 may be formed to have a cavity 484 and a protrusion 482. The at least one LED 402 may transmit light towards the imaging lens 404, wherein the imaging lens 404 may direct, refract and/or reflect the light towards the body tissue 490. The imaging lens 404 may not have to be in direct contact with the body tissue 490. The light may be absorbed by the body tissue, as in FIGS. 4A and 4B. The light absorbed may scatter as illustrated with the at least one scatter path 486. The imaging lens 404 or more particularly the cavity 484 may receive the scattered light form from the body tissue 490, and refract the light towards the protrusion 482. Even though not shown in FIG. 4D, the protrusion 482 may refract light towards the detector 406. The light may then be received by the detector 406.

In an embodiment, the at least one LED 402 is positioned farther from the center of the lens 404 compared to at least one of the protrusion 482, cavity 484, as shown in FIG. 4D. Thus, the at least one LED 402 may be situated on the edge area of the lens 404, for example. At least one of the cavity 484, protrusion 482 may be situated substantially at the vertical axis of the lens 404, wherein the vertical axis may be substantially perpendicular to the body tissue 490.

In an embodiment, the optical heart activity sensor 312 and/or the apparatus of FIG. 3, comprises an Extended Depth of Field (EDOF) member 488. The EDOF member 488 may increase the focus depth of the optical heart activity sensor 312. Thus, the measurement of the optical heart activity sensor 312 may be accurate for different depths of the body tissue. Therefore, the effect of the spatial shifts may be decreased by comparing measurements from different depths and selecting the measurement(s) which have the lowest effect of the spatial shifts. Further, by comparing the measurements, the effect of the spatial shifts may be detected, and thus decreased.

Still referring to FIG. 4D, the cavity 484 and/or the protrusion 482 may be polarized and/or comprise a polarization member similar to the at least one polarization member 408. The benefit of using the polarization member(s) may be that the polarization reduces reflections causing error(s) to the measurement. By using polarization member(s), the light received by the detector 406 may be substantially light that has propagated through the body tissue 490 along a scatter path, such as the at least one scatter path 486. Further, polarized light may be used to detect orientation of blood particles, such as red cells, in the blood. Thus, when a heartbeat changes orientation of the blood particles, the change may be detected with the polarized light. The change may be detectable in a scatter pattern(s) produced by the light to the detector 406.

Figure 4E:
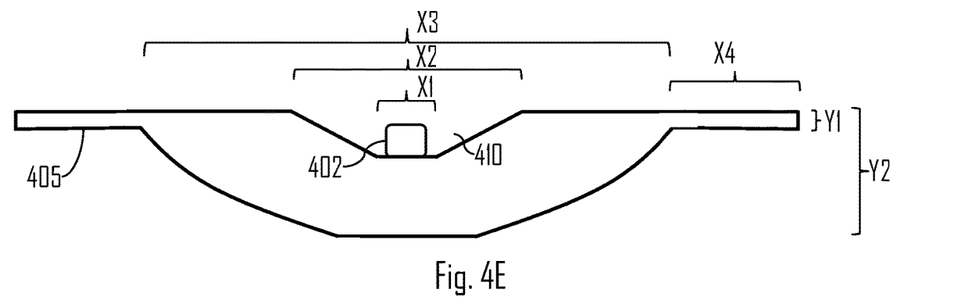

FIG. 4E illustrates an embodiment of the invention. Referring to FIG. 4E, the imaging lens 404 may have thickness of Y2. The imaging lens 404 may comprise a flange 405 around the optical axis. The flange 405 may enable the imaging lens 404 to collect light from a larger area of the body tissue. The flange's 405 thickness may be Y1 and width X4. The width of the bottom of the cavity 410 may be X1, and width of the top of the cavity 410 may be X2. The width of the imaging lens 404 may be X3+X4+X4.

In an embodiment, the X1 is substantially around 1.6 mm.
In an embodiment, the X2 is substantially around 5.0 mm.
In an embodiment, the X3 is substantially around 10.8 mm.
In an embodiment, the X4 is substantially around 2.6 mm.
In an embodiment, the Y1 is substantially around 0.64 mm.
In an embodiment, the Y2 is substantially around 2.4 mm.

Figure 4F:
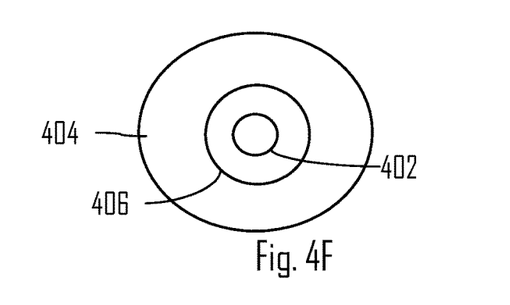

FIG. 4F illustrates an embodiment of the invention. Referring to FIG. 4F, the optical heart activity sensor 312 may be illustrated from a bird's eye view. As shown in FIG. 4F, the elements 402, 404, 406 may be substantially round. The at least one LED 402 may transmit light towards the body tissue and the imaging lens 404 may collect scattered light from the body tissue, and direct it to the detector 406. This may be done on a circle area.

In an embodiment, the detector 406 may be as wide as the top part of the cavity 410. This may enable the light to be collected from a desired area around the at least one LED 402. Further, using the mirror coating in the cavity 410 may prevent the light transmitted by the at least one LED 402 to directly hit the detector 406, without first propagating through the body tissue 490.

In an embodiment, the at least one LED 402 comprises a Red Green Blue (RGB) LED. The RGB LED may transmit red, green and blue wavelengths. It is possible that the RGB LED transmits different wavelengths in pulses.

In an embodiment, the imaging lens 404 is arranged to at least partially surround the at least one LED 402. The imaging lens 404 may further encapsulate the at least one LED 402 against the body tissue 490. If the cavity 410 is filled, the at least one LED 402 may be encapsulated by the imaging lens 404 and the filling.

In an embodiment, FIG. 4A illustrates an optical configuration comprising the at least one LED 402, the imaging lens 404 and the detector 406. The optical configuration may further comprise the cavity 410, and/or the one or more polarizing members 408. Embodiments described in relation to FIGS. 4A to 4F may be applicable with said embodiment describing said optical configuration. For example, said optical configuration may comprise the EDOF member 488 and/or the flanges 405.

In an embodiment, FIG. 4D illustrates an optical configuration comprising the at least one LED 402, the imaging lens 404 and the detector 406. The optical configuration may further comprise the cavity 484, the protrusion 482, and/or the one or more polarizing members 408. Embodiments described in relation to FIGS. 4A to 4F may be applicable with said embodiment describing said optical configuration. For example, said optical configuration may comprise the EDOF member 488 and/or the flanges 405.

Figure 5A:
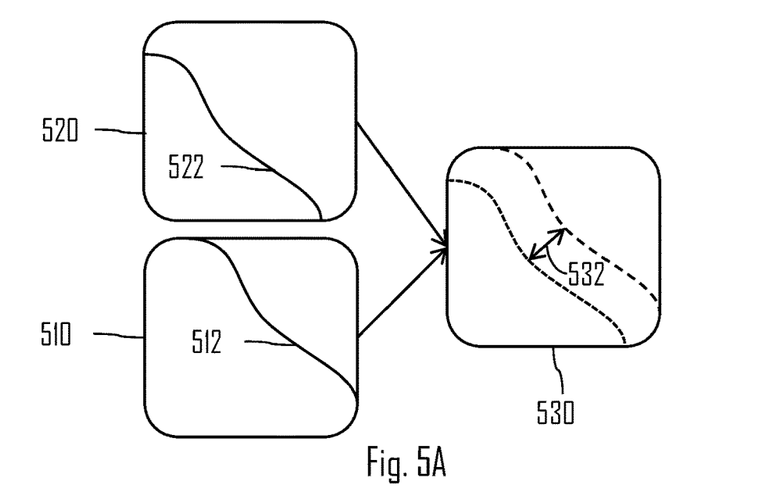
FIGS. 5A to 5B illustrate some embodiments of the invention.

FIG. 5A illustrates an embodiment of the invention. As was described earlier the imaging lens 404 may form the instantaneous images on the detector 406 from the received light. At a certain time the instantaneous image formed on the imaging lens may be understood as a sample of the optical heart activity measurement. The processing circuitry 306 of FIG. 3 may be configured to receive the samples from the detector 406, wherein each of the samples illustrates a detected image, by the detector 406, at a certain time. Further, if the EDOF member 488 is used, the samples may be received from the EDOF member 488. Also, the samples may be processed by the optical heart activity sensor 312 before reaching the processing circuitry 306. In such case, the optical heart activity sensor 312 may comprise processing circuitry for processing the instantaneous images and/or the samples before transmitting them to the wrist device 102 or similar device.

In an embodiment, the optical heart activity sensor 312 combines two or more instantaneous images that have been detected at different parts of the detector 406 at substantially same time. These combined instantaneous images may form a sample and/or a combined instantaneous image that may be obtained by the wrist device 102. These combined instantaneous images may be obtained by the wrist device 102 in sequence, and further the heart activity data may be formed based on the combined instantaneous images. Even further, the combined instantaneous images may be compared and/or combined to determine the effect of the spatial shifts. Therefore, the instantaneous images, introduced in relation to FIG. 2, may be combination of detections at same time from different spots and/or areas on the detector 406 and/or combination of detections performed in a sequence.

Referring to FIG. 5A, a first instantaneous image 510 and a second instantaneous image 520 are shown. The instantaneous images 510, 520 may comprise information 512, 522 from which the heart activity of the user 100 may be determined by the processing circuitry 306. The processing circuitry 306 may, for example, detect blood fluctuation changes from the instantaneous images, and determine heart rate of the user based on said information.

In an embodiment, the instantaneous images 510, 520 are received simultaneously by the detector 406. The Instantaneous images 510, 520 may then correspond to certain spots on the detector 406. This may be possible in case that the detector 406 comprises and/or is a matrix detector which functionality is close to that of a camera.

The instantaneous images 510, 520 may comprise pixel information comprising intensity, color and/or identity of at least one pixel of the instantaneous images. The pixel information may be used to find the detector 406 area(s) and/or pixels on which the received instantaneous image is as good as possible. Therefore, the effect of the spatial shifts may be decreased by selecting the area(s) on which the received light is as good as possible.

In an embodiment, the processing circuitry 306 determines the effect of the spatial shifts, at least partly, by determining and/or detecting spatial differences between the instantaneous images detected by the detector 406. This may be achieved by comparing the information 512, 522 between the instantaneous images 510, 520, for example.

In an embodiment, the determining spatial differences between the instantaneous images 510, 520 comprises: combining, by the processing circuitry 306, the instantaneous images 510, 520, and determining the spatial differences between the instantaneous images 510, 520 based on the combining. The combined result 530 may reveal the effect of the spatial shifts 532. For example, the detector 406 may detect the spatial shifts 532 by utilizing a reference point in the body tissue, such as blood veins, moles and differentiations in skin color. The spatial shifts 532 may then be detected as the logical position of the reference point on the detector 406 may change. The effect of the spatial shift may be shown with arrow 532 in FIG. 5A. The enhancing of the instantaneous images may be based on the reference point also. For example, the controller 308 may virtually reposition instantaneous images that have been determined to have effect caused by the spatial shifts. Virtual relocating may mean that after the digital processing, the reference points are at the same locations in the virtual representations of the instantaneous images. Thus, the effect of the spatial shifts may be decreased, and the heart activity data may be formed more effectively by the processing circuitry 306.

In an embodiment, at least one of the compared instantaneous images is a comparing instantaneous image to which other instantaneous images are compared against. The comparing instantaneous image may be an average of instantaneous images which have produced an acceptable heart activity measurement result, for example. Thus, by comparing the first instantaneous image 510 against the comparing instantaneous image, spatial differences and/or changes may be observed and the effect of the spatial shifts revealed.

In an embodiment, the processing circuitry 306 determines the effect of the spatial shifts, at least partly, by comparing at least the first and the second instantaneous images 510, 520 detected by the detector 406, wherein the first instantaneous image 510 is formed from a first radiation component and the second instantaneous image 520 is formed from a radiation component, and wherein the first and the second radiation components have different wavelengths. In such case the different wavelengths may act differently in terms of propagation depth and/or distance. From these differences effect of the spatial shifts may be determined, at least partly. Naturally, more than two instantaneous images may be used. Further, more than one wavelength of light may be used in the process.

Still referring to FIG. 5A, the processing circuitry 306 may process the received instantaneous images, such as the instantaneous images 510, 520, in to the combined result 530. The instantaneous images 510, 520 may reveal when the logical spot of the image formed on the imaging lens 404 changes. As said before, the processing circuitry 306 may use previous information about the received instantaneous images to determine effect of the spatial shifts in the received instantaneous images 510, 520.

Figure 5B:
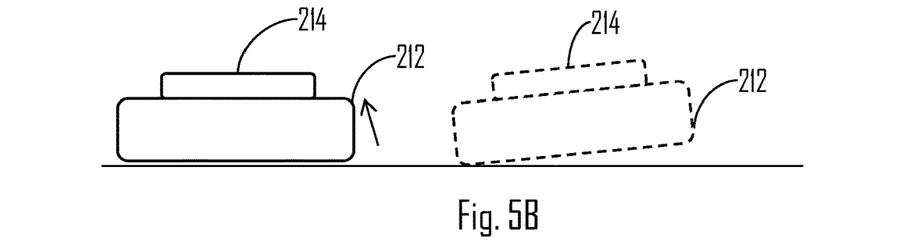

FIG. 5B illustrates an embodiment of the invention. Referring to FIG. 5B, the motion sensor 314, comprised in the at least one sensor 310, may be configured to measure the spatial shifts of an apparatus, such as the wrist device 102 and/or the external sensor device(s), in relation to the body tissue of the user 100. More precisely, the motion sensor 314 may be configured to detect the spatial shifts of the measurement head of the optical heart activity sensor 312 in relation to the body tissue of the user. The motion sensor 314 may detect, for example, if the optical heart activity sensor 312 tilts. This information about the tilting may be used by the processing circuitry 306 to determine, at least partly, the effect of the spatial shifts in the heart activity data.

In an embodiment, the processing circuitry 306 determines the effect of the spatial shifts based, at least partly, on the spatial shifts detected by the motion sensor.

Figure 6A:
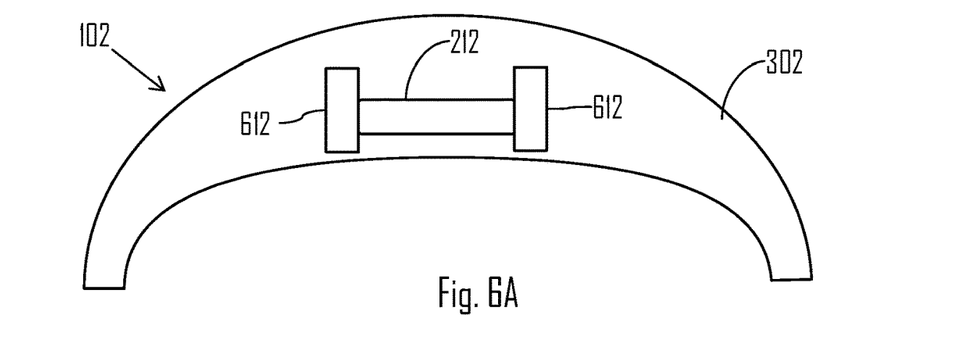
FIGS. 6A to 6B illustrate some embodiments of the invention.
Figure 6B:
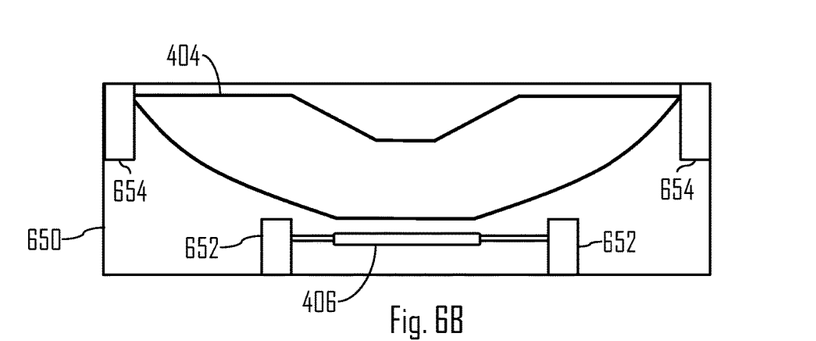

Let us now look closer on how the effect of the spatial shifts may be decreased by looking at the embodiments of FIGS. 6A and 6B. Referring to FIG. 6A, the wrist device 102 may comprise at least one actuator 612 for moving the optical heart activity sensor 312 to decrease the effect of the spatial shifts according to instructions from the controller 308. Naturally, similar actuator(s) may be used with external sensor device(s) 104. In such case, the controller 308 may transmit the instructions to the actuator(s), for example, by wireless connection. Therefore, the actuator(s) may be controlled from the portable electronic device 106, for example.

In an embodiment, the at least one actuator 612 is used to control the position of the optical heart activity sensor 312 in order to alter the depth of the measurement. This may be beneficial if, for example, in cold conditions the optical heart activity sensor 312 should be closer to the body tissue of the user 100.

Referring to FIG. 6B, the at least one actuator 652, 654 may be used to move different parts of the optical heart activity sensor 312. The imaging lens 404 may be moved by the actuator 654. The actuator 654 may tilt the imaging lens 404, change horizontal, and/or vertical position of the imaging lens 404. Similarly, the actuator 652 may move the detector 406. Therefore, for example if it is determined by the processing circuitry 306 that the optical heart activity sensor 312 is not in straight line against the body tissue, the controller 308 may use the actuator(s) 652, 654 to change the angle of the imaging lens 404 and the detector 406 in order to decrease the effect of the spatial shifts of the heart activity measurement. In a way, the actuator(s) 652, 654 may be understood as a means for keeping the optical heart activity sensor 312 in place and resisting forces causing the effect of the spatial shifts. Further, the actuators 652, 654 and the at least one actuator 612 may be seen as means for modifying optical configuration of the optical heart activity sensor, thus modifying optical path of the received light.

In an embodiment, the wrist device 102 comprises at least one actuator for modifying optical path of the received light, in order to decrease the effect of the spatial shifts, according to instructions from the controller 308.

Figure 7:
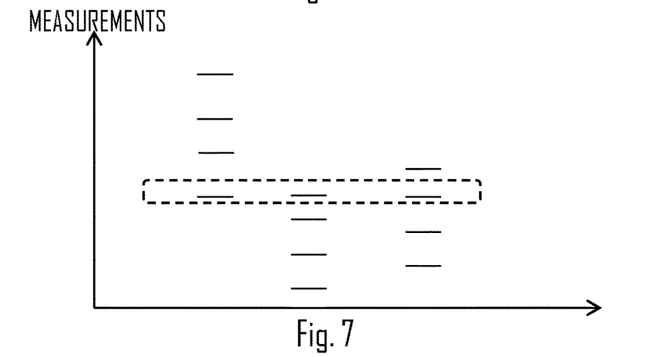
FIG. 7 illustrates an embodiment of the invention.

FIG. 7 illustrates an embodiment of the invention. Referring to FIG. 7, three measurement sets are illustrated with each set comprising four lines. Each set may represent a measurement performed with a certain wavelength different from each other. By using different colors, the processing circuitry 306 may determine from the measurements which values represent the actual heart activity, such as heart rate of the user 100. In the example of FIG. 7, the heart rate may be determined to be in the area of the dash line, as other values may be determined to be caused by effect of the spatial shifts and/or faulty measurement. It needs to be noted that the example of FIG. 7 may be rather brute example, and actual implementation(s) may be more complex. The idea of the example is to illustrate the using of different colors to decrease and/or remove the effect of the spatial shifts.

In an embodiment, the controller 308 is configured to decrease the effect of the spatial shifts by digital processing. One example of this may be the use of EDOF member 488. Another example may be to use at least one algorithm to reduce the effect of the spatial shifts. The at least one algorithm may be based on decreasing the effect of the spatial shifts using input from different wavelengths. Also, digital processing may be used to, for example, spatially shift sample and/or instantaneous image information in order to reduce the effect of the spatial shifts. For example, if two or more instantaneous images are combined, the effect of spatial shifts between the two or more instantaneous images may be detected based on the details of the instantaneous images. The details may comprise body tissue details, such as blood veins and/or moles. The controller 308 may then digitally move the instantaneous images so that they are spatially corresponding to each other. This may mean that after the digital processing, the instantaneous images are spatially similar, and therefore the effect of the spatial shifts may be decreased, and even canceled. Thus, the heart activity data, formed from the instantaneous images, may be enhanced. The spatially similar may mean that details of the body tissue are on same virtual positions between the consecutive instantaneous images.

For example, if the measurement head moves 1 millimeter (mm) which causes corresponding effect on at least one instantaneous image, the controller 308 may digitally process the at least one instantaneous image so that the effect caused by the 1 mm movement of the measurement head is decreased. The digitally processing in this case may mean that contents of the at least one instantaneous image are digitally repositioned, wherein the amount of digital repositioning corresponds to the 1 mm movement of the measuring head. The digital movement may be to opposite direction compared to the movement of the measurement head.

Figure 8:
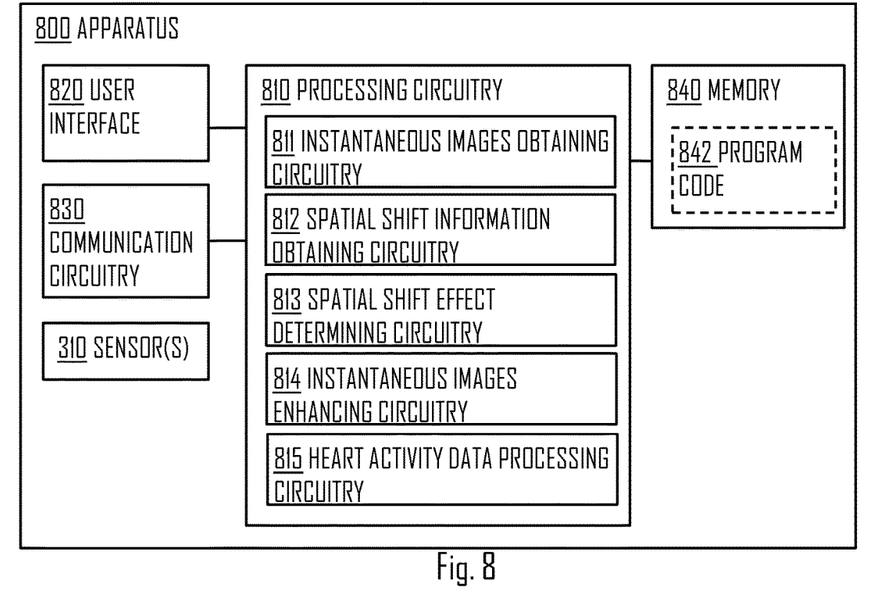
FIG. 8 illustrates a block diagram of an apparatus according to an embodiment of the invention.

FIG. 8 illustrates a block diagram of an apparatus according to an embodiment of the invention. Referring to FIG. 8, the apparatus 800 may be the wrist device 102, the external sensor device(s) 104, the portable electronic device 106 and/or the server 114.

In an embodiment, the apparatus 800 comprises at least one processor and at least one memory 840 comprising a computer program code 842, wherein the at least one memory 840 and the computer program code 842 may be configured, with the at least one processor, to perform the above-mentioned functions of the apparatus 800, such as the steps of FIG. 2.

The apparatus 800 may comprise a wireless communication circuitry 830 configured to enable the apparatus 800 to communicate with other devices. For example, in the case that the portable electronic device performs the steps of FIG. 2, the instantaneous images, and other relating data, may be received from the external sensor device(s) 104. The wireless communication circuitry 830 may be based on Bluetooth® specifications, e.g. Bluetooth Low Energy, and/or Near-Field-Communication (NFC) technology, wherein the NFC technology may enable data transfer on short distances. However, the wireless communication circuitry 830 may not be limited to these technologies.

In an embodiment, the apparatus 800 comprises the at least one sensor 310 comprising the optical heart activity sensor 312, such as a PPG sensor, and/or the motion sensor(s) 314. Therefore, the apparatus 800 may be capable of performing the heart activity measurement by itself.

Still referring to FIG. 8, the apparatus 800 may comprise a user interface 820 enabling interaction, by the user, with the apparatus 800. The user interface 820 may comprise physical button(s), display(s), touch-screen(s), speaker(s) and/or microphone(s) to name a few.

In an embodiment, the apparatus 800 comprises a processing circuitry 810. The processing circuitry 810 may comprise an instantaneous images obtaining circuitry 811 configured to obtain instantaneous images from the optical heart activity sensor 312, wherein the instantaneous images characterize the heart activity data of the user 100, a spatial shift information obtaining circuitry 812 configured to obtain information about spatial shifts of the measuring area, such as the measuring head, the of the optical heart activity sensor in relation to the body tissue of the user 100, a spatial shift effect determining circuitry 813 configured to determine effect of the spatial shifts in the instantaneous images based on the information about the spatial shifts, an instantaneous images enhancing circuitry 814 configured to enhance the instantaneous images by decreasing the effect of the spatial shifts in the instantaneous images, and a heart activity data processing circuitry 815 configured to process the enhanced instantaneous images into the heart activity data of the user 100.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIGS. 1 to 7 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of FIGS. 1 to 7 or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of FIGS. 1 to 7, or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 1 to 7 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. An apparatus for measuring heart activity data of a user, the apparatus comprising:
at least one sensor comprising an optical heart activity sensor, wherein the optical heart activity sensor comprises a measuring head and a matrix detector, wherein the measuring head is configured to be directed towards a body tissue of the user and to form instantaneous images on the matrix detector from a light propagated through the body tissue of the user, wherein the matrix detector is configured to detect the instantaneous images, and wherein the at least one sensor is further configured to detect spatial shifts of the measuring head in relation to the body tissue of the user;
a processing circuitry configured to receive the instantaneous images from the optical heart activity sensor, to determine effect of the spatial shifts in the instantaneous images based on the detected spatial shifts, and to process the instantaneous images into the heart activity data of the user; and
a controller configured to enhance the heart activity data by decreasing the effect of the spatial shifts in the instantaneous images,
wherein the measuring head comprises a plurality of light emitting diodes configured to transmit light into the body tissue of the user, and an integral imaging lens adapted to be arranged to at least partially surround and encapsulate each light emitting diode of the plurality of light emitting diodes against body tissue of the user and configured to receive the light propagated through the body tissue of the user, wherein the imaging lens is configured to form the instantaneous images on the matrix detector from the received propagated light,
wherein the imaging lens comprises at least one parabolic reflector structure having a curved reflective surface, wherein each light emitting diode of the plurality of light emitting diodes is within a cavity of the at least one parabolic reflector structure, wherein the imaging lens is configured to receive the light propagated through the body tissue of the user, to average the received propagated light and to direct the received propagated light to the matrix detector to form the instantaneous images on the matrix detector from the received propagated light, and wherein the at least one parabolic reflector structure is configured to direct the received propagated light to the matrix detector.

2. The apparatus of claim 1, wherein the light transmitted by the plurality of light emitting diodes comprises two or more wavelengths.

3. The apparatus of claim 2, wherein the processing circuitry determines the effect of the spatial shifts, at least partly, by comparing at least a first instantaneous image and a second instantaneous image detected by the matrix detector, wherein the first instantaneous image is formed from a first radiation component and the second instantaneous image is formed from a second radiation component, and wherein the first and the second radiation components comprise light having different wavelengths compared to each other.

4. The apparatus of claim 1, wherein the plurality of light emitting diodes is configured to transmit the light into the body tissue of the user in pulses.

5. The apparatus of claim 1, wherein the optical heart activity sensor comprises at least one polarizer arranged to polarize at least one of the transmitted light into the body tissue of the user and the received light propagated through the body tissue of the user.

6. The apparatus of claim 1, wherein the processing circuitry determines the effect of the spatial shifts, at least partly, by determining spatial differences between the instantaneous images detected by the matrix detector.

7. The apparatus of claim 6, wherein the determining spatial differences between the instantaneous images comprises:
    combining the instantaneous images; and
    determining the spatial differences between the instantaneous images based on the combining.

8. The apparatus of claim 1, wherein the at least one sensor comprises a motion sensor, and wherein the motion sensor is configured to detect the spatial shifts of the measurement head in relation to the body tissue of the user.

9. The apparatus of claim 8, wherein the processing circuitry determines the effect of the spatial shifts based, at least partly, on the spatial shifts detected by the motion sensor.

10. The apparatus of claim 1, further comprising:
    at least one actuator for modifying optical path of the received light, in order to decrease the effect of the spatial shifts, according to instructions from the controller, wherein the actuator at least one of tilts the imaging lens, changes horizontal position of the imaging lens, changes the vertical position of the imaging lens according to instructions from the controller.

11. The apparatus of claim 1, wherein the controller is configured to decrease the effect of the spatial shifts by digital processing.

12. A method comprising:
    obtaining, by an apparatus, instantaneous images from an optical heart activity sensor, wherein the instantaneous images characterize a heart activity data of a user, wherein the optical heart activity sensor comprises a measuring head and a matrix detector, wherein the measuring head is configured to be directed towards a body tissue of the user and to form the instantaneous images on the matrix detector from a light propagated through the body tissue of the user, wherein the matrix detector is configured to detect the instantaneous images, and wherein the optical heart activity sensor is further configured to detect spatial shifts of the measuring head in relation to the body tissue of the user;
    obtaining information about the spatial shifts of a measuring area of the optical heart activity sensor in relation to the body tissue of the user;
    determining effect of the spatial shifts in the instantaneous images based on the information about the spatial shifts;
    enhancing the instantaneous images by decreasing the effect of the spatial shifts in the instantaneous images; and
    processing the enhanced instantaneous images into the heart activity data of the user,
    wherein the measuring head comprises a plurality of light emitting diodes configured to transmit light into the body tissue of the user, and an integral imaging lens adapted to be arranged to at least partially surround and encapsulate each light emitting diode of the plurality of light emitting diodes against the body tissue of the user and configured to receive the light propagated through the body tissue of the user, wherein the imaging lens is configured to form the instantaneous images on the matrix detector from the received propagated light,
    wherein the imaging lens comprises at least one parabolic reflector structure having a curved reflective surface, wherein each light emitting diode of the plurality of light emitting diodes is within a cavity of the at least one parabolic reflector structure, wherein the imaging lens is configured to receive the light propagated through the body tissue of the user, to average the received propagated light and to direct the received propagated light to the matrix detector to form the instantaneous images on the matrix detector from the received propagated light, and wherein the at least one parabolic reflector structure is configured to direct the received propagated light to the matrix detector.

13. The method of claim 12, wherein the obtaining information about the spatial shifts comprises determining spatial differences between the instantaneous images received from the optical heart activity sensor.

14. The method of claim 13, wherein the determining spatial differences between the instantaneous images comprises:
    combining the instantaneous images; and
    determining the spatial differences between the instantaneous images based on the combining.

15. The method of claim 13, wherein the effect of the spatial shifts is determined, at least partly, by comparing at least a first and a second instantaneous images received from the optical heart activity sensor, wherein the first instantaneous image is formed from a first radiation component and the second instantaneous image is formed from a second radiation component, and wherein the first and the second radiation components comprise light having different wavelengths compared to each other.

16. The method of claim 12, wherein the information about the spatial shifts is, at least partly, obtained from a motion sensor.

17. The method of claim 16, wherein the effect of the spatial shifts is determined, at least partly, from the information about the spatial shifts obtained from the motion sensor.

18. The method of claim 12, further comprising:
    delivering instructions to the optical heart activity sensor causing the optical heart activity sensor to modify optical configuration of the optical heart activity sensor in order to decrease the effect of the spatial shifts.

19. The method of claim 12, further comprising:
    decreasing the effect of the spatial shifts by digital processing.

20. A non-transitory computer-readable medium comprising program instructions encoded thereon that, when executed by an apparatus, perform a method comprising:
    obtaining, by the apparatus, instantaneous images from an optical heart activity sensor, wherein the instantaneous images characterize a heart activity data of a user;

obtaining information about spatial shifts of a measuring area of the optical heart activity sensor in relation to a body tissue of the user;
determining effect of the spatial shifts in the instantaneous images based on the information about the spatial shifts;
enhancing the instantaneous images by decreasing the effect of the spatial shifts in the instantaneous images; and
processing the enhanced instantaneous images into the heart activity data of the user,
wherein the optical heart activity sensor comprises a measuring head and a matrix detector, wherein the measuring head is configured to be directed towards the body tissue of the user and to form the instantaneous images on the matrix detector from a light propagated through the body tissue of the user, wherein the matrix detector is configured to detect the instantaneous images, and wherein the optical heart activity sensor is further configured to detect the spatial shifts of the measuring head in relation to the body tissue of the user,
wherein the measuring head comprises a plurality of light emitting diodes configured to transmit light into the body tissue of the user, and an integral imaging lens adapted to be arranged to at least partially surround and encapsulate each light emitting diode of the plurality of light emitting diodes against body tissue of the user and configured to receive the light propagated through the body tissue of the user, wherein the imaging lens is configured to form the instantaneous images on the matrix detector from the received propagated light,
wherein the imaging lens comprises at least one parabolic reflector structure having a curved reflective surface, wherein each light emitting diode of the plurality of light emitting diodes is within a cavity of the at least one parabolic reflector structure, wherein the imaging lens is configured to receive the light propagated through the body tissue of the user, to average the received propagated light and to direct the received propagated light to the matrix detector to form the instantaneous images on the matrix detector from the received propagated light, and wherein the at least one parabolic reflector structure is configured to direct the received propagated light to the matrix detector.

* * * * *